United States Patent
Willis

(10) Patent No.: US 6,357,279 B1
(45) Date of Patent: Mar. 19, 2002

(54) CONTROL CIRCUIT FOR THERMAL CONDUCTIVITY CELL

(75) Inventor: Peter M. Willis, Benton Harbor, MI (US)

(73) Assignee: Leco Corporation, St. Joseph, MI (US)

( * ) Notice: Subject to any disclaimer, the term of this patent is extended or adjusted under 35 U.S.C. 154(b) by 0 days.

(21) Appl. No.: 09/772,021

(22) Filed: Jan. 29, 2001

(51) Int. Cl.[7] .............................................. G01N 25/18
(52) U.S. Cl. ..................................................... 73/25.03
(58) Field of Search .......................... 73/25.03; 422/96, 422/97

(56) References Cited

U.S. PATENT DOCUMENTS

| | | |
|---|---|---|
| 2,926,520 A | 3/1960 | Schmauch |
| 3,449,951 A | 6/1969 | Westersten |
| 3,512,080 A | 5/1970 | Hanson |
| 3,683,671 A | 8/1972 | Van Swaay |
| 3,793,525 A | 2/1974 | Burch et al. |
| 3,864,959 A | 2/1975 | MacDonald |
| 3,886,786 A | 6/1975 | Hoppesch et al. |
| 4,057,755 A | 11/1977 | Piesche |
| 4,164,862 A | 8/1979 | Jackson |
| 4,258,563 A | 3/1981 | Yasuda et al. |
| 4,384,934 A | 5/1983 | de Bruin et al. |
| 4,461,166 A | 7/1984 | Gatten et al. |
| 4,498,330 A | 2/1985 | Hosoya |
| 4,533,520 A | 8/1985 | Bossart et al. |
| 4,541,988 A | 9/1985 | Tozier et al. |
| 4,594,879 A | 6/1986 | Maeda et al. |
| 4,649,745 A | 3/1987 | Kondo et al. |
| 4,685,325 A | 8/1987 | Warchol |
| 4,735,082 A | 4/1988 | Kolloff |
| 4,741,198 A | 5/1988 | Farren et al. |
| 4,829,810 A | 5/1989 | Anderson et al. |
| 4,850,714 A | 7/1989 | Wiegleb |
| 4,856,319 A | 8/1989 | Golay |
| 4,872,339 A | 10/1989 | Gerhard et al. |
| 4,918,974 A | 4/1990 | Hachey et al. |
| 4,992,724 A | 2/1991 | Hisanaga et al. |
| 4,996,431 A | 2/1991 | Bonne et al. |
| 5,081,869 A | 1/1992 | Hachey et al. |
| 5,113,143 A | 5/1992 | Wei |
| 5,233,308 A | 8/1993 | Willis |
| 5,369,278 A | 11/1994 | Lehto |
| 5,379,630 A | 1/1995 | Lacey |
| 6,114,700 A | 9/2000 | Blades |

FOREIGN PATENT DOCUMENTS

| | | |
|---|---|---|
| EP | 0745840 | 12/1996 |
| JP | 4-54451 A | 2/1992 |

OTHER PUBLICATIONS

Copy of application Serial No. 09/307,111 entitled Switched Mode NDIR System.

*Primary Examiner*—Robert Raevis
(74) *Attorney, Agent, or Firm*—Price, Heneveld, Cooper, DeWitt & Litton

(57) ABSTRACT

A control circuit for a thermal conductivity cell employs a constant resistance bridge drive circuit which automatically adjusts to maintain a measurement filament at a constant resistance. A reference filament provides a differential signal representative of the concentration of an analyte. A detection circuit utilizes digital/analog methods to significantly reduce 1/f noise of an amplifier providing at least a seven fold improvement in signal-to-noise ratio. The circuit also includes a bridge nulling method adjusted under microprocessor control to eliminate manual offset adjustments. A reference protection circuit is coupled to the reference filament and prevents the voltage applied to the filaments from overheating the filaments in the event there is a breach in the gas flow path.

3 Claims, 6 Drawing Sheets

CONTROL CIRCUIT FOR THERMAL CONDUCTIVITY CELL

BACKGROUND OF THE INVENTION

The present invention relates to a control circuit for a thermal conductivity cell and particularly one which provides linearity, lower noise, and filament protection.

A variety of constant resistance thermal conductivity detector circuits exist which employ a single filament in the leg of a Wheatstone bridge. A servo loop forces the bridge to balance, thereby holding the filament at a constant resistance. With such a system, however, the single filament is subject to significant drift since there is no reference filament and the output is sensitive to the temperature of the thermal conductivity cell block. Further, the signal can suffer from non-linearities inasmuch as the thermal conductivity is proportional to the power dissipated and the voltage across the filament. Sensitivity suffers inasmuch as a high common mode output signal to drive the bridge is necessary, and, therefore, gain cannot be applied to the output signal to increase the sensitivity of the cell. Finally, without a reference filament, the effects due to vibrations and pressure variations are apparent in the output signal.

Attempts have been made to control drift by altering the filament resistance between two temperatures resulting in a differential signal independent of block temperature. Other approaches have employed a bridge control signal alternated between constant resistance and constant voltage resulting in a similar differential control signal. In some approaches, drift has been compensated for by attaching a temperature sensor to the cell block itself. The linearity problem has also been addressed utilizing a closed-loop analog circuit in most cases. In some instances, a resistance loop is closed employing a digital signal and comparator to sense an imbalance in the microprocessor controlled D-to-A converter to drive the bridge back to balance. These configurations have the advantage of having a linear output verses concentration as the pulse width is directly related to power dissipated in the filament.

The sensitivity of a detection system utilizing a thermal conductivity cell has been addressed by various analog methods, typically including the utilization of a voltage divider and switch capacitor network to reference the voltage across each resistor to a common ground. The sensitivity of such a system is somewhat improved over other methods, however, the sensitivity is still limited to about 2 ppm (parts per million) detection. The problem with pressure disturbances in a thermal conductivity system has been addressed as well in which two measurement filaments and two reference filaments have been employed in a four filament bridge in an effort to control the average resistance of the bridge to compensate for such pressure disturbances.

Thus, although the prior art has attempted to address individually each of the various problems inherent in a thermal conductivity detection system, the prior art has not solved each of the problems adequately nor comprehensively addressed these problems in an overall system which provides improved linearity, low noise, and a protected thermal conductivity system in which the thermal conductivity resistance filament is protected from oxidation. There exists, therefore, a need for an improved thermal conductivity control circuit which provides these advantages.

SUMMARY OF THE INVENTION

The system of the present invention provides a control circuit for a thermal conductivity cell by employing a constant resistance bridge drive circuit which automatically adjusts to accommodate various carrier gases, such as helium and argon. Additionally, a reference filament is placed in a third leg of the bridge to provide a differential measurement signal. The detection circuit utilizes digital/analog methods to significantly reduce 1/f noise of an amplifier providing at least a seven fold improvement in signal-to-noise ratio. This also eliminates the thermocouple effects in the path from the bridge to the amplifier.

The circuit includes a bridge nulling method which is adjusted under microprocessor control to eliminate the need for manual offset adjustments. Thus, the typical necessity of matching the measurement and reference filaments can be relaxed, thereby reducing the cost of a thermal conductivity cell employing such a control circuit. The automatic monitoring of the bridge filament can warn the operator when filaments have aged and require replacement. The reference filament is monitored individually and protected against exceeding its oxidation temperature. This system compensates for fluctuation in cell block temperature, exhaust pressure variations, and improves the linearity more than ten fold over conventional detection bridges.

These features and advantages of the present invention are embodied in a system in which reference and measurement filaments are incorporated in a Wheatstone bridge and a constant resistance circuit compares the bridge drive voltage applied to the bridge divided in half in a closed-loop feedback circuit to maintain the measurement filament a constant resistance. Signals from the reference detector are modulated at a frequency above the significant 1/f noise frequency of an amplifier in a preferred embodiment of the invention, amplified, demodulated, and filtered to provide a low noise output signal representative of the concentration of a sample gas through the measurement cell.

According to another aspect of the invention, the reference filament drive is continually adjusted for changes in relative resistance between the reference filament and the measurement filament by a null adjustment circuit coupled to the reference filament and to the bridge drive circuit. Output signals are coupled to a microprocessor for controlling the null adjustment to null any differences between the resistive legs of the bridge prior to an analysis. According to another aspect of the present invention, a reference protection circuit is provided and is coupled to the reference filament and controls the voltage applied to the filament through a voltage divider and integrator circuit to prevent overheating of the reference electrode in the event there is a breach in the gas flow path or other event which otherwise would allow the filament to overheat.

In the most preferred embodiment of the invention, each of the circuits are integrated in an overall control system for a thermal conductivity cell including measurement and reference electrodes to provide a highly sensitive detection system which is extremely linear and reliable over time. These and other features, objects and advantages of the present invention will become apparent upon reading the following description thereof together with reference to the accompanying drawings.

DESCRIPTION OF THE PREFERRED EMBODIMENT

Figure 1:
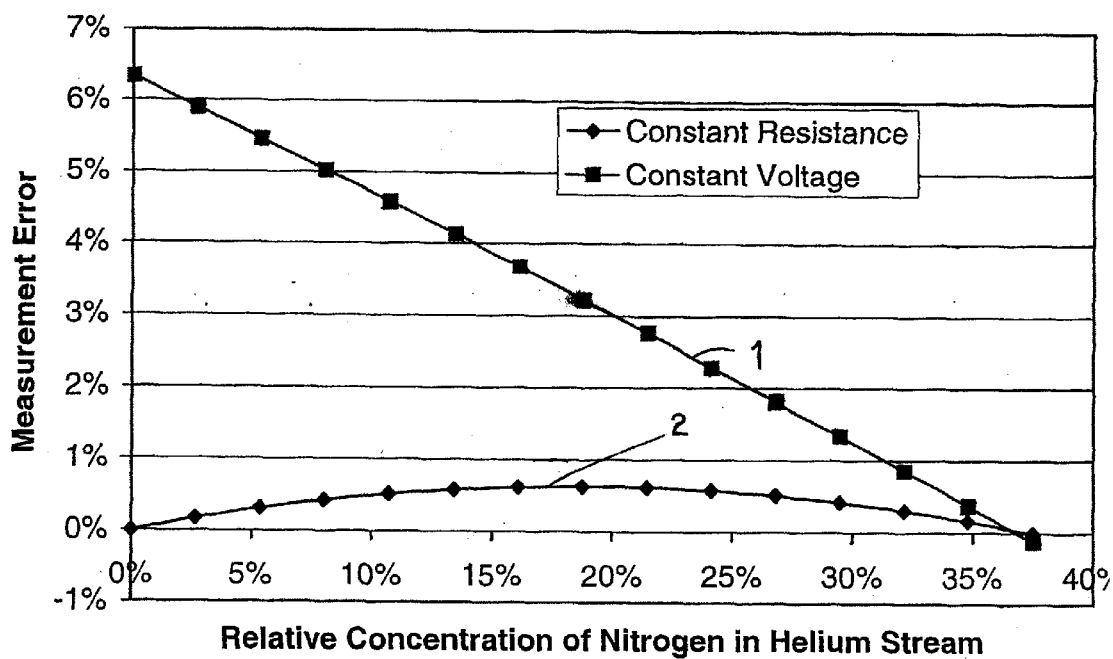
FIG. 1 is a representative graph showing the linearity of an existent constant voltage bridge circuit as opposed to the linearity of the constant resistance system of the present invention.

Referring initially to FIG. 1, there is shown empirical test results showing the linearity errors between a prior art constant voltage bridge drive thermal conductivity cell with the concentration on the X axis and the measurement error from a thermal conductivity cell on the Y axis. As can be seen at lower concentrations, the output signal 1 has a 3% to 6% error. Line 2 in FIG. 1, on the other hand, shows the concentration of an analyte verses output signal obtained by the constant resistance thermal conductivity system of the present invention, showing that with varying concentrations of an analyte, the detected output signal is substantially error free.

Figure 2:
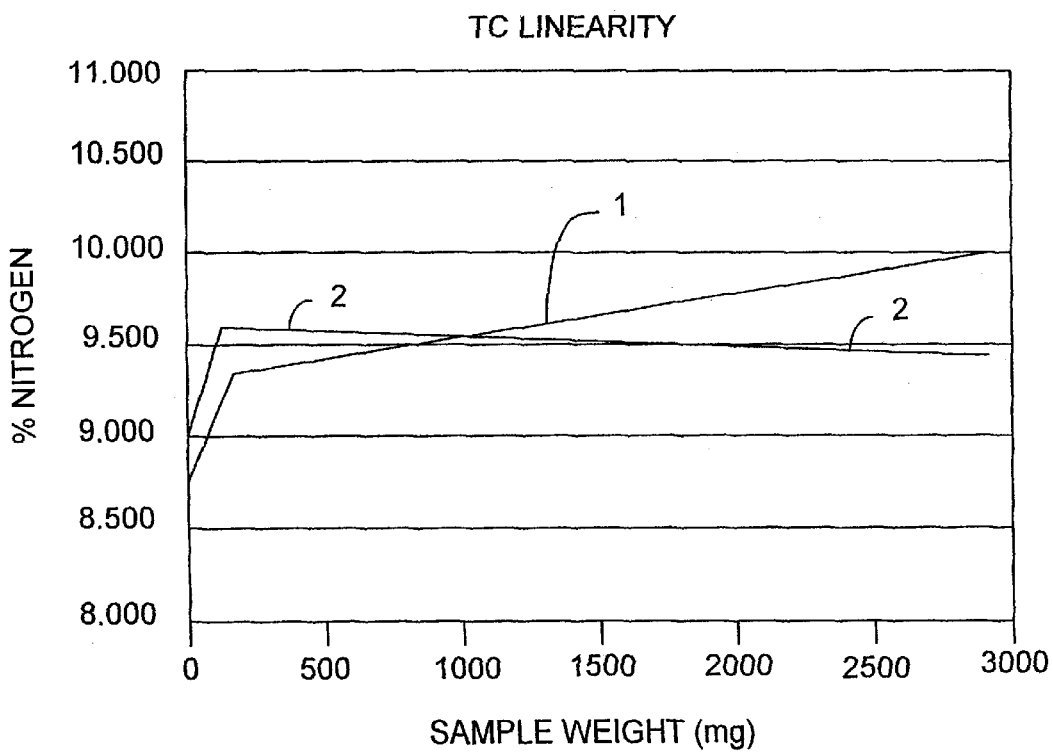
FIG. 2 is a graph of a sample with nitrogen having different sample weights showing the constant output results achieved by the system of the present invention for different weights of samples as compared to the variations which occur with systems of the prior art.

FIG. 2 shows the linearity of the output shown by line 2 of the constant resistant system of the present invention as opposed to line 1 of the prior art constant voltage thermal conductivity cell system for varying sample weights having the same sample concentration of nitrogen. As can be seen by comparing line 2 with line 1, the constant resistance system represented by the present invention provides a substantially flat sample concentration of 9.5% nitrogen for weights varying from 10 mg to nearly 3 g, whereas the prior art constant voltage thermal conductivity system provides significant variations of from 9.3% to 10% for the same sample concentration. Further, the sensitivity of the thermal conductivity system of the present invention and its noise immunity features provide a sensitivity for detecting an analyte with a concentration as low as 100 parts per billion with a linearity of better than a 0.1%. These dramatically improved results for the use of a thermal conductivity cell in an analyzer for analytes, such as nitrogen and hydrogen or other analytes combusted in a furnace, is achieved utilizing the thermal conductivity cell and control system discussed initially in connection with FIG. 3.

Figure 3:
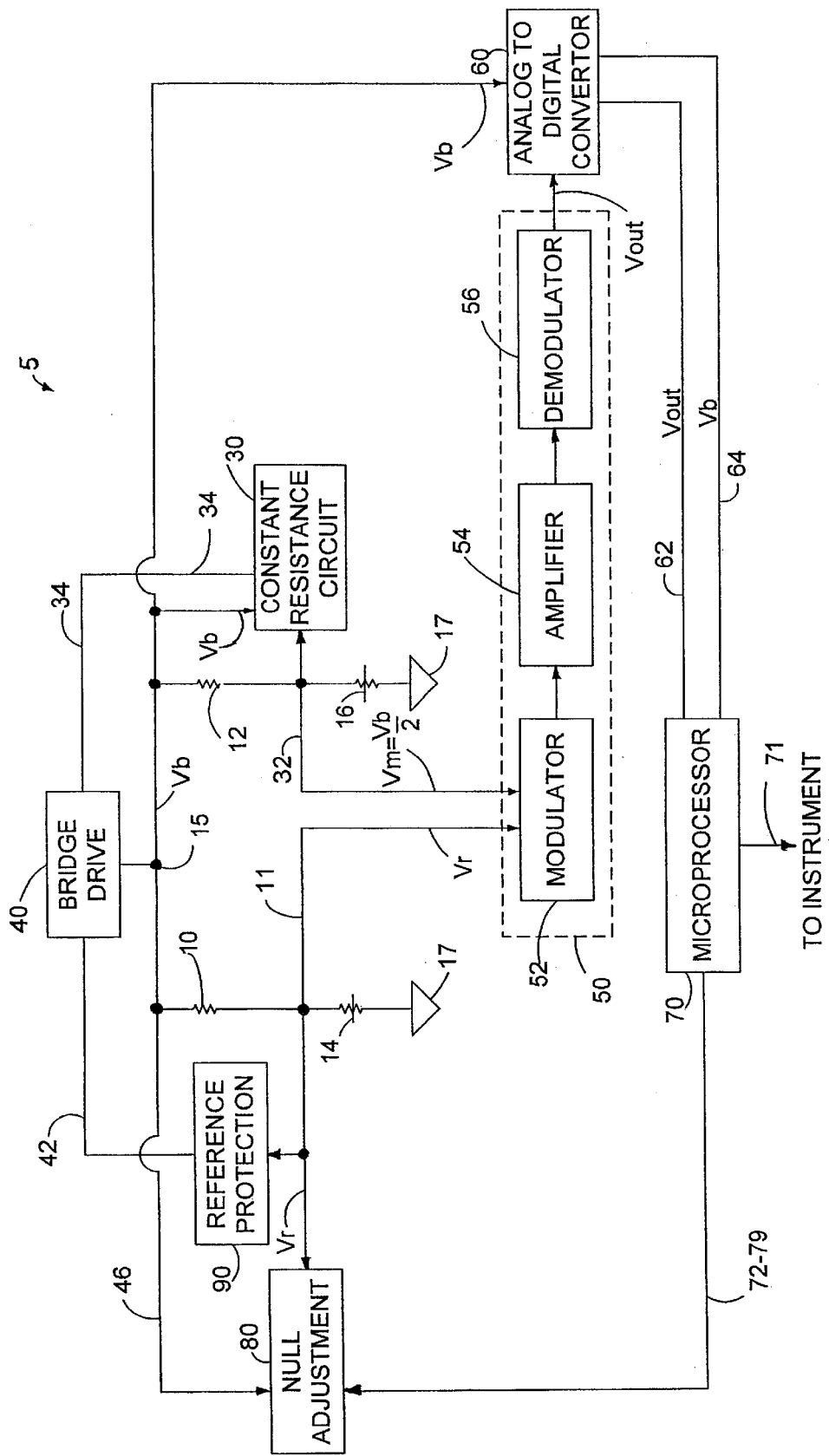
FIG. 3 is a circuit diagram partly in block and schematic form of the system of the present invention.

In FIG. 3, there is shown a control circuit 5 for controlling the operation of a thermal conductivity cell including a reference filament 14 and a measurement filament 16 coupled in a convention Wheatstone bridge configuration with a precision resistor 10 and precision resistor 12, respectively, having one node 15 coupled to a bridge drive circuit 40 and an opposed node 17 coupled to system ground. The reference and measurement filaments 14 and 16, respectively, are platinum wires, in turn, mounted in a thermally controlled block heated to a constant temperature falling within the range of from about 45° C. to about 50° C. Resistors 10, 12 are 90 ohm 0.1% precision resistors and the target resistance of the platinum filaments 14, 16 of the reference and measurement filaments, respectively, is 90 ohms at the operating temperature.

During an analysis, a combustion furnace is employed and a carrier gas, such as helium, is supplied to the reference cell 14 and the combined carrier gas and analyte flows through the measurement cell 16 such that the voltage across the reference filament 14, which is coupled to the same voltage node 15 as filament 16 through the precision resistors 10, 12, typically will be somewhat less than the voltage across the measurement cell 16, with an analyte present due to the greater cooling of the reference filament 14 by helium. The measurement filament 16 resistance is held substantially constant by constant resistance circuit 30 which is coupled to the bridge drive in a closed-loop feedback circuit, described in detail in connection with FIG. 4 below, to maintain the resistance and, therefore, temperature of the filament 16 constant with varying analytes. The respective voltages $V_r$ across reference filament 14 and $V_m$ across measurement filament 16 are then applied to a noise reducing modulator/demodulator circuit 50 resulting in an output signal $V_{out}$ applied to an analog to digital converter circuit 60. Circuit 60 is a dual channel A/D converter which receives an input $V_b$ (from the bridge drive circuit) and converts both signals to digital output signals at conductor 62 for $V_{out}$ and conductor 64 for $V_b$ to a microprocessor 70, which as described in greater detail below, provides an output signal at output 71 coupled to the instrument which controls the furnace, display and printed output of the sample analysis information detected by circuit 5. Microprocessor 70 also provides parallel digital control signals on conductors 72–79 to a null adjustment circuit 80 for balancing any resistance differences between filaments 14 and 16 initially and due to aging and assuring that the $V_{out}$ signal remains positive. The $V_r$ signal is also applied to a reference protection circuit 90 which monitors the $V_r$ signal to apply a control signal to bridge drive 40 via conductor 42 to protect the reference filament from oxidation due to overheating in the event the gas flow path is opened or the carrier gas supply is exhausted.

Thus, circuit 5 (FIG. 3) of the present invention provides multiple functions, namely, maintaining the platinum measurement filament 16 at a constant resistance during an analysis (to improve the linearity of the output signal); modulating and demodulating and detecting the difference signal between the reference filament and measurement filament in a circuit to improve the sensitivity and noise reduction of the resultant output signal; a null adjustment to control for initial differences in the platinum filament resistances as well as compensating for aging; and protection for the reference and measurement filaments in the event of gas flow interruption. The details of the operation of the circuit shown in FIG. 3 is best understood by reference to the remaining circuit diagrams beginning with the constant resistance circuit of FIG. 4, showing also the details of the bridge drive circuit 40.

Figure 4:
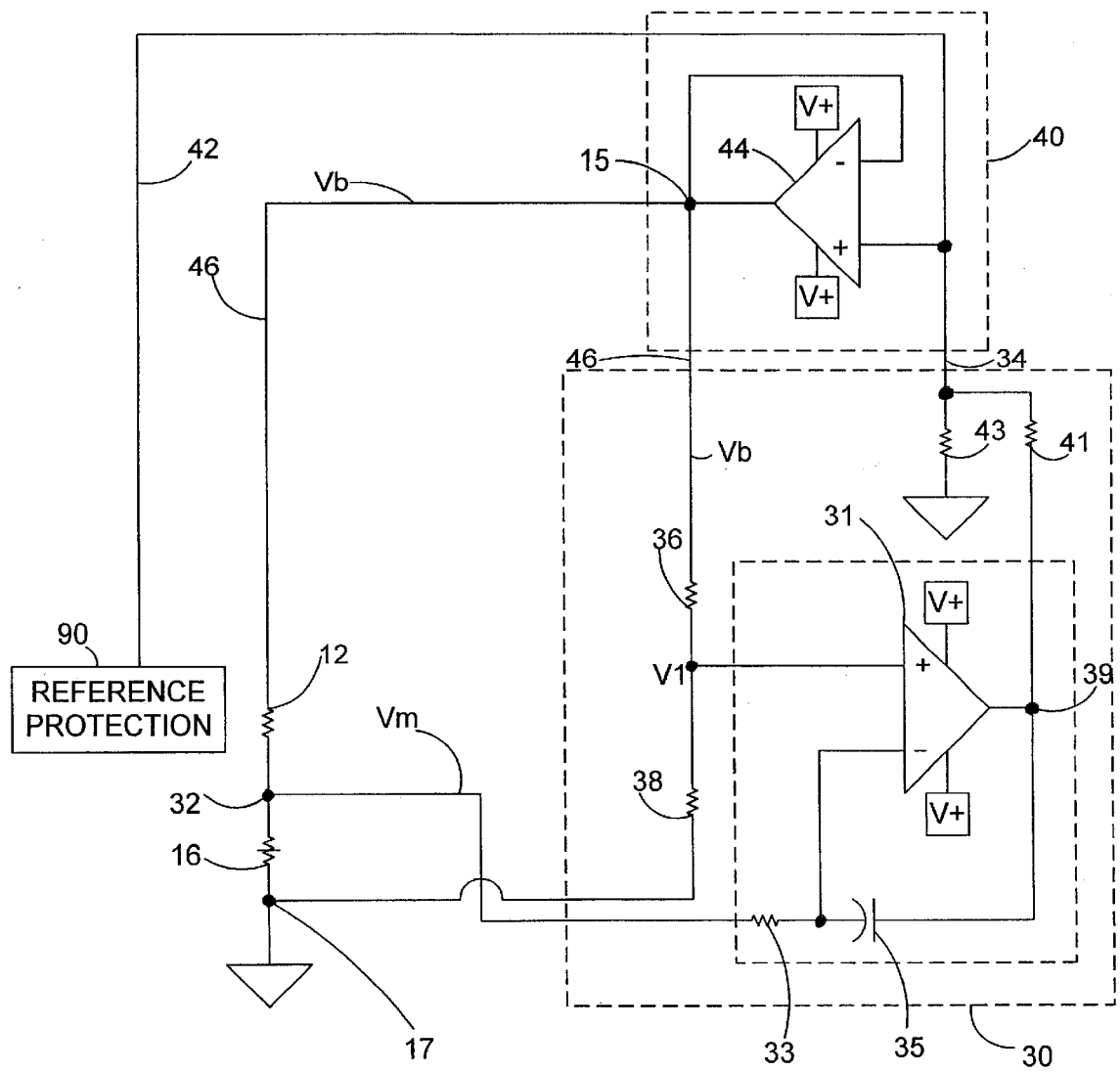
FIG. 4 is a detailed schematic diagram of part of the system shown in FIG. 3.

In FIG. 4, the resistor 12 and its associated measurement filament 16 of the Wheatstone bridge is shown. The junction at node 32 is coupled to one input of an operational amplifier 31 of constant resistance circuit 30 by means of an integrator with an input resistor 33 and capacitor 35. The junction of 33, 35 is coupled to one input of operational amplifier 31 and capacitor 35 coupled between input 33 and output 39. Amplifier 31 receives a second input $V_1$ from a voltage divider comprising resistors 36 and 38 coupled in series between the bridge drive node 15 and ground node 17. Resistors 36, 38 are equal value precision resistors and, in the preferred embodiment, 1 KOhm 1% resistors. Thus, the voltage $V_1$ equals $V_b/2$, while the single $V_m$ will attempt to vary as analyte flows through the thermal conductivity cell including filament 16. As $V_m$ tends to change, itts signal is integrated and compared by amplifier 31 which provides a control output signal at its output terminal 39 through a resistive divider network including sesistor 41 and resistor 43 with a junction 34 thereof coupled to the input of an operational amplifier 44 forming the bridge drive circuit 40 with its remaining input coupled to its output as a unity gain amplifier. Thus, as $V_m$ tends to change, the feedback loop signal on input terminal 34 to amplifier 44 will tend to lower or raise $V_b$ to maintain the voltage at a level such that $V_m$ equals $V_1$ due to the feedback including the integrator circuit. The bridge drive circuit amplifier 44 also receives a signal from reference protection circuit 90 on conductor 42 which, if necessary, will override the $V_m$ signal in a situation where protection of the reference filament is necessary, as will be described in connection with FIG. 7 below.

Typically, $V_1$ for a helium carrier in an analyte will be approximately 5 volts. In the event $V_m$ drops, the drive applied to the bridge drive circuit 40 will be increased through the feedback loop to boost the voltage, keeping $V_b$ at a level which maintains the temperature and, therefore, resistance of filament 16 at 90 Ohms, equaling that of resistance 12. As seen in FIG. 3, $V_m$, therefore, equals $V_b/2$, which tends to be relatively constant. The signal $V_m$ is constant for a given concentration of an analyte supplied to the thermal conductivity cell. The reference filament will have a different voltage $V_r$, typically lower than $V_m$, due to more cooling by being exposed to the carrier gas, such as helium, and the respective signals $V_r$ and $V_m$ are applied to the modulator/demodulator circuit 50 for processing to amplify and detect the resultant output signal $V_{out}$, which represents the concentration of an analyte to be detected.

The linearity of the signal $V_{out}$, which is achieved by the constant resistance circuit 30, is shown by the following equations:

Filament Resistance

The resistances of the measure and reference filaments are temperature dependent according to the following equation:

$$R=R_0*(1+\alpha*(T_R-T_0))$$

Where
R: Filament resistance
$R_0$: Reference resistance (70 ohm) at $T_0$
$T_0$: Reference temperature=25° C.
$\alpha$: Coefficient of resistance=0.0043 ohms/° C.
$T_R$: Temperature of the filament

Heat Conduction

Heat is transferred away from the heated filament to the cell block at a rate described by the following equation:

$$Q_R=V_R^2/R-K*(T_R-T_B)$$

Where
$Q_R$: Heat transfer (W)
$V_R$: Voltage across filament (V)
K: Thermal conductivity of gas (W/° C.)
$T_B$: Temperature of cell block (° C.)

Thermal Conductivity of a Binary Gas Mixture

When two gases of differing thermal conductivity are mixed, the resulting thermal conductivity is described by the following equation:

$$K_M=K_R*(1+E*C_M)$$

Where
$K_M$: Thermal conductivity (TC) of the gas mixture (W/° C.)
$K_R$: TC of the reference carrier gas (W/° C.)
E: Equivalency factor relating the TC of the reference gas to the TC measurement gas
$C_M$: Relative concentration of measurement gas in gas mixture

Derivation of Linearity for Constant Resistance Bridge

Electrical Equations for Constant Resistance Bridge

The circuit of FIG. 4 adjusts the bridge voltage, $V_B$, to maintain the resistance of the measurement TC filament constant at 90 ohms. The reference filament will change its resistance as the bridge voltage is varied. The voltage across the reference filament is then:

$$V_{Rr}=V_B*R_R/(R_R+R_M)$$

Where
$R_R$: Resistance of the reference filament
$R_M$: Resistance of the measurement filament=90 ohms
$V_{Rr}$: Voltage across the reference filament
$V_B$: Bridge voltage
Solving equation (4) for $V_B$:

$$V_B=V_{Rr}*(R_R+R_M)/R_R$$

Solving equation (1) for $T_R$ and substituting into equation (2) yields the following equation for reference voltage:

$$V_R=\sqrt{(K_R*R_R*(A*R_R+B))}$$

Where $$A=1/(*R_0)$$

$$B=1/+T_0+T_B$$

Equivalently, the equation for the measure side voltage, $V_{Rm}$, is:

$$V_{Rm}=V_B/2=\sqrt{(K_M*R_M*(A*R_M+B))}$$

Solving equation (7) for $K_M$:

$$K_M=V_B^2/(4*R_M*(T_{Rm}-T_B))$$

Solving equation (3) for $C_M$:

$$C_M=(K_M/K_R-1)/E$$

By combining equations (5), (6), (8), and (9), the concentration of the analyte, $C_M$, can be expressed as a function of the reference resistance, $R_R$ $$C_M=\{[K_R*R_R*(A*R_R)*(R_M+R_R)^2]/[4R_R^2*R_M*K_R*(T_{Rm}-T_B)]-1\}/E$$

The output voltage from the cell is simply the difference between the voltages across the reference and measurement filaments:

$$V_0=V_{Rm}-V_{Rr}$$

From these equations, FIG. 1 plots the linearity error in $V_0$ vs. $C_M$ as compared to the linearity error in a constant voltage bridge application.

Figure 5:
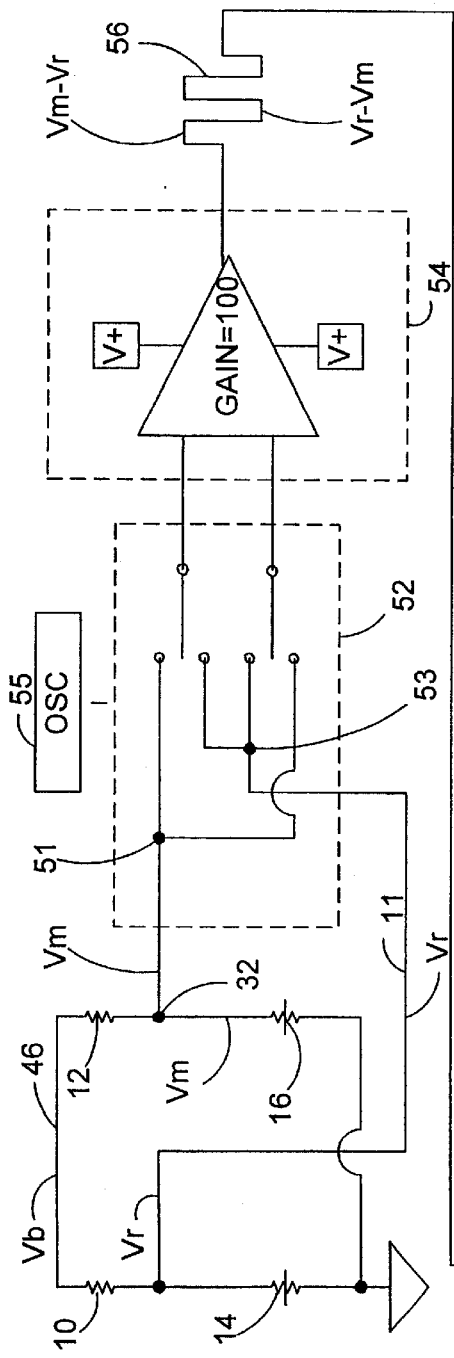
FIG. 5 is a detailed schematic view of the modulator/demodulator circuit shown in FIG. 3.
Figure 5:
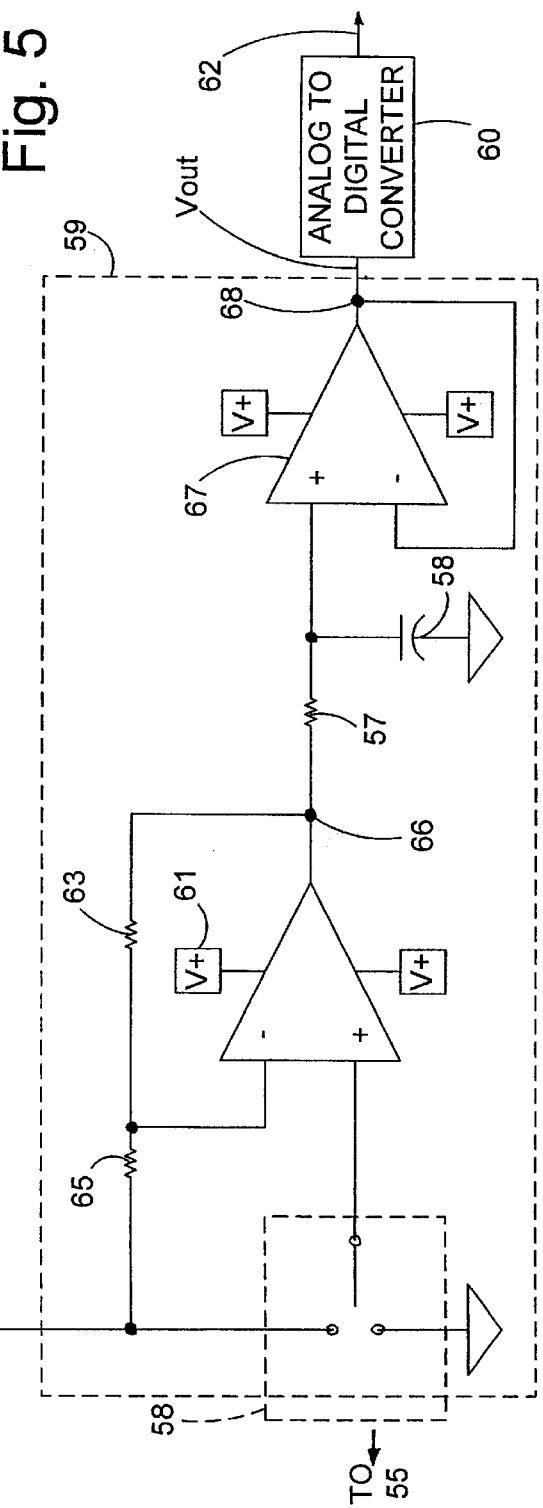

In FIG. 5, the Wheatstone bridge circuit is shown and the $V_m$ signal on conductor 32 is applied to an input terminal 51 of a low resistance solid state switch 52, while signal $V_r$ is applied to terminal 53 of the switch, which is schematically represented as a double pole, double throw switch in FIG. 5. The switch 52 is a commercially available AGD433, which is coupled to a 1 kHz oscillator 55 also coupled to a second solid state switch 58 for synchronizing switches 52 and 58. Switch 52 operates at a frequency of 1 kHz, thereby alternately chopping and applying $V_m$ and $V_r$ to a 100 gain amplifier 54 resulting in a square wave output signal shown as waveform 56 having a positive peak equal to $V_m-V_r$ and a negative peak equal to $V_r-V_m$, as amplified by amplifier 54. The peaks typically will be a maximum of about 20 mV while the 1/f noise can be a few hundred nV. By chopping the signals $V_m$ and $V_r$ at 1 kHz, the 1/f noise inherent in the amplifier 54 can be eliminated by the demodulator 59 shown in FIG. 5.

Signal 56 is applied to switch 58, which alternately applies the positive and negative signals to one terminal of operational amplifier 61 having a feedback resistor 63 between its output and its remaining input and an input resistor 65 coupling signals 56 to such remaining input. The resultant signal at output terminal 66 constitutes a positive DC output signal, which includes some high frequency components filtered out by a low pass filter constituting resistors 57 and capacitor 58 which, in a preferred embodiment, was a 100 k resistor and a 2.2 microfarad capacitor. Thus, only signal frequency (0–2 Hz) signals representative of the analyte concentration are applied to the input of buffer amplifier 67. Amplifier 67 provides essentially a DC output signal $V_{out}$ at output terminal 68 which is applied to one input channel of the analog-to-digital converter 60 for providing a 24 bit digital output signal at output conductor 62 representative of the signal $V_{out}$.

The A-to-D converter 60 operates at an approximately 100 ms sampling period to provide a 24 bit output signal on bus 62 applied to microprocessor 70, which applies the $V_{out}$ signal to the analytical instrument in a conventional fashion via bus 71. In one embodiment, the thermal conductivity control circuit 5 can be used in an instrument such as a TC-436 instrument manufactured by Leco Corporation of St. Joseph, Mich. The A-to-D converter 60 also provides a 24 bit signal representative of $V_b$ on conductor 64 which is detected by the microprocessor and employed to compensate for the temperature of the thermal conductivity block. Thus, if the block temperature changes, $V_b$ will change and microprocessor 70 also receives temperature control information from the thermal conductivity cell block and is programmed to apply a correction factor to the $V_{out}$ which varies as a function of the temperature of the block as represented by the $V_b$ signal.

Figure 6:
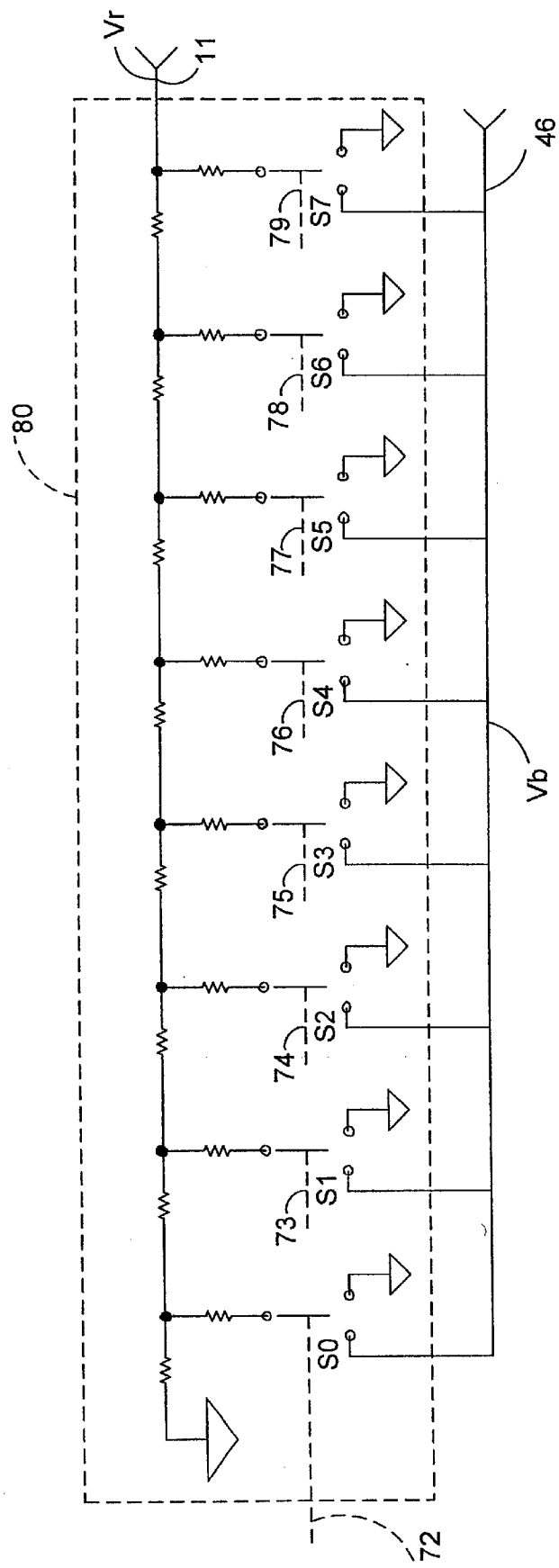
FIG. 6 is a detailed schematic view of the null adjustment circuit shown in FIG. 3.

The null adjustment circuit 80 is employed to balance the initial differences between filament resistance 14 and measurement resistance 16 by injecting onto node 11 a voltage which is digitally selected by a network shown in FIG. 6 under the control of microprocessor 70. Also, this adjustment assures that the $V_{out}$ signal remains positive so it can be processed by A/D circuit 60 and typically will run between 0.2 and 2 volts in a normal system. The microprocessor 70 provides eight lines of output 72–79 which are coupled to solid state switches S0–S7 of an R2R resistive ladder network circuit 80 as shown in FIG. 6. Each of the eight bits drives a different one of the digital switches from the microprocessor 70, which in a preferred embodiment is an Intel 8051 microprocessor. The R2R network 80 looks at the parallel bits and each of the switches (which are AGD433 devices), depending upon the voltage $V_{out}$ detected by microprocessor 70, maintains the ratio of resistance 10 over reference filament 14 the same as the ratio of resistance 12 over measurement filament 16. The microprocessor 70 thus receives a $V_{out}$ input signal on line 62 and through a conventional trapezoidal convergence function program provides parallel bit drive signals to the resistor ladder network 80 during the time when the carrier gas is flowing through both the measurement and reference filaments of the thermal conductivity cell system. If $V_{out}$ is too high, the switches S0–S7 are initially adjusted relatively full on to lower the injected signal to $V_r$ on node 11 by coupling node 11 to ground and/or through a selected group of resistors. As the $V_{out}$ signal decreases, the switches are gradually switched to the $V_b$ state until such time as the signal is below 2 volts. If the signal is below 0.2 volts, the ladder network is switched under the microprocessor control to increase the signal injected to the node 11 by coupling more of the switches selectively in sequence to the $V_b$ bus 46. This process typically is conducted initially to compensate for the differences in resistance between filaments 14 and 16. Once the resistive ladder has been programmed through the microprocessor, typically it need not be changed except with aging of the filaments 14 and/or 16 or in the event the $V_{out}$ signal becomes too low.

Figure 7:
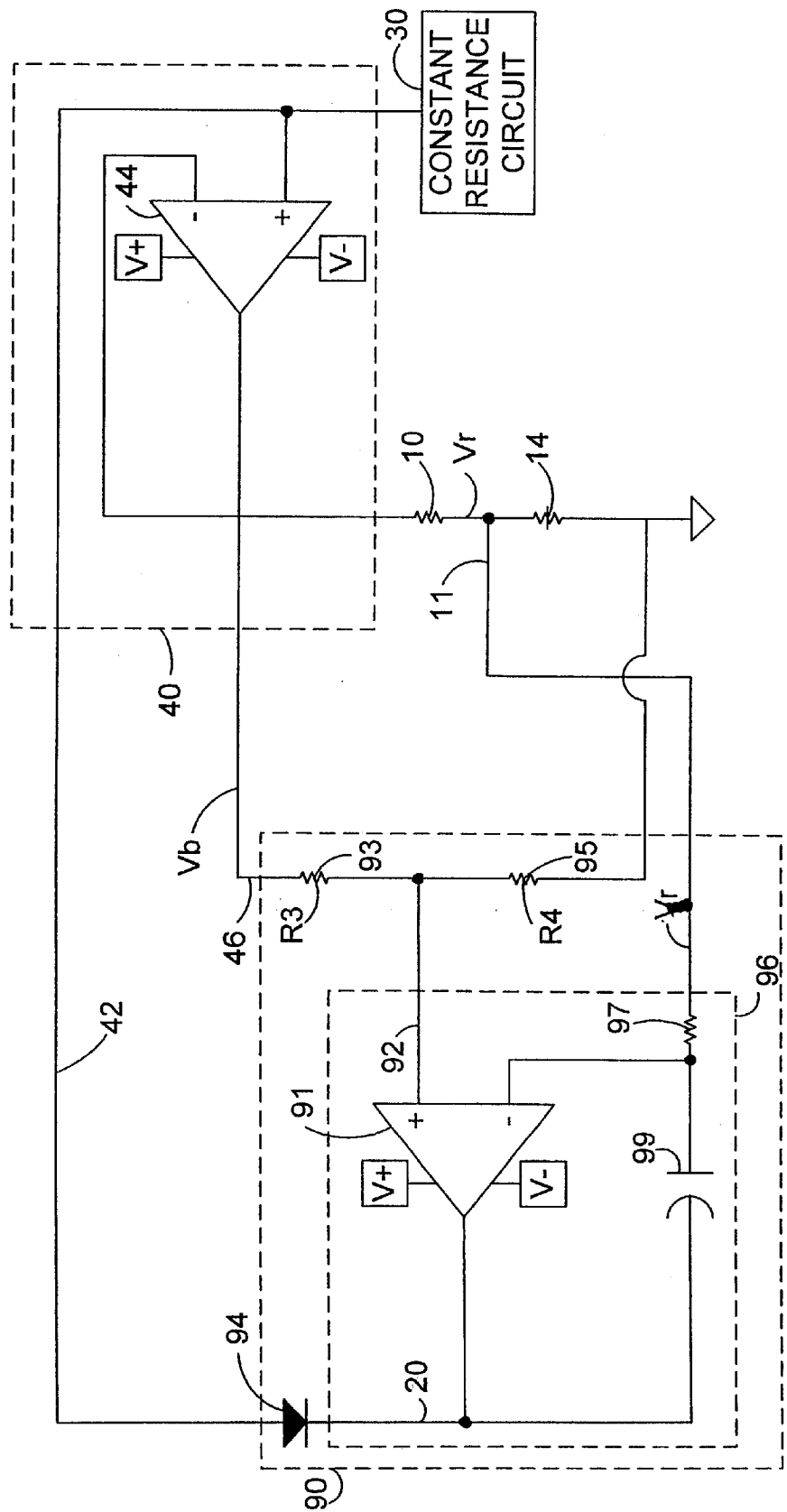
FIG. 7 is a detailed schematic view of the reference protection circuit shown in FIG. 3.

In order to protect filaments 14, 16, reference protection circuit 90 is provided which is shown in detail in FIG. 7. Circuit 90 provides a signal to the bridge drive circuit 40 which, in the event the reference filament tends to overheat and, therefore, may oxidize, will reduce the drive voltage $V_b$ until the cause of the overheating situation is corrected. Typically, this would occur in the event of an interruption of carrier gas flow or an inadvertent opening of the flow path.

Circuit 90 comprises a clamping diode 94 coupled to the output of an operational amplifier 91, which receives an input signal along conductor 92 which is a voltage $V_b$ divided by resistive voltage divider including resistors 93 and 95. Resistor 95 has a slightly greater value than resistor 93, such that a signal is, therefore, provided which is somewhat higher than $V_b/2$ at input 92 to amplifier 91. $V_r$, on the other hand, is applied to the remaining input of the operational amplifier 91 through an integrator including resistor 97 and capacitor 99. Typically, resistor 93 will be a 1 kOhm resistor and resistance 95 is selected to be a 1.2 kOhm resistor. In the event the carrier gas flow is interrupted and the resistance filament 14 increases, $V_r$ exceeds the artificially increased $V_b/2$ signal at conductor 92, the output of amplifier 91 will drop, allowing diode 94 to conduct, thereby clamping the input signal at the positive input of operational amplifier 44 in the bridge drive circuit 40 to a lower voltage, thus reducing $V_b$ to a level at which the temperature of the filaments 14 and 16 will not oxidize. Typically during normal operation, the voltage at the output of amplifier 91 will be higher than the signal at the positive input terminal of amplifier 44 and diode 94, therefore, the reference protection circuit 90 will have no effect on the control of $V_b$ by the constant resistance circuit 30. If, however, the resistance of the reference filament 14 increases due to overheating, the bridge drive voltage $V_b$ will be reduced to a level which prevents oxidation of the reference filaments 14 and 16.

As can be seen by one skilled in the art, the various circuits can be employed individually or collectively in the overall circuit as shown, for example, in circuit 5 in FIG. 3 to provide an improved thermal conductivity cell control circuit which has extremely high linearity, low noise, and which controls for aging of the filaments as well as protecting filaments from oxidation.

It will become apparent to those skilled in the art that various modifications to the preferred embodiment of the invention as described herein can be made without departing from the spirit or scope of the invention as defined by the appended claims.

The invention claimed is:

1. A thermal conductivity cell drive circuit for a thermal conductivity detection system employing a Wheatstone bridge, wherein said drive circuit comprises:

a variable voltage source for coupling to the Wheatstone bridge having a reference filament and a measurement filament, said voltage source applying a drive voltage to the bridge; and a constant resistance circuit coupled to said variable voltage source and to a measurement filament of the Wheatstone bridge for providing control signals to said variable voltage source control the drive voltage applied to the measurement filament to maintain the measurement filament at a constant resistance and detecting the voltage between said reference filament and said measurement filament to provide a signal representative of the concentration of an analyte, wherein said constant resistance circuit comprises a voltage divider coupled from the output of said variable voltage source for dividing the drive voltage, an integrator circuit coupled to receive the divided voltage said integrator circuit further coupled to the measurement filament and responsive to the divided voltage and the voltage from the measurement filament for adjusting the control signal applied to said variable voltage source to maintain the voltage across the measurement filament equal to the divided drive voltage.

2. The circuit as defined by claim 1 wherein said integrator circuit includes an operational amplifier with an RC circuit coupled between one input thereof and an output and wherein the remaining input thereof is coupled to said voltage divider.

3. The circuit as defined by claim 2 wherein said voltage divider comprises a pair of serially coupled equal value resistances.

* * * * *

UNITED STATES PATENT AND TRADEMARK OFFICE
CERTIFICATE OF CORRECTION

PATENT NO. : 6,357,279 B1
DATED : March 19, 2002
INVENTOR(S) : Peter M. Willis

It is certified that error appears in the above-identified patent and that said Letters Patent is hereby corrected as shown below:

Column 1,
Line 38, "verses" should be -- versus --.

Column 3,
Line 15, before "DESCRIPTION" insert -- DETAILED --.
Line 25, "verses" should be -- versus --.
Line 54, "convention" should be -- conventional --.

Column 4,
Line 63, "1KOhm 1% resistors" should be -- 1 KOhm 0.1% resistors --.
Line 66, "itts" should be -- its --.

Column 5,
Line 2, "sesistor 41" should be -- resistor 41 --.
Line 53, "$Q_R=V_R^2/R-K*(T_R-T_B)$" should be -- $Q_R=V_R^2/R=K*(T_R-T_B)$ --.

Column 8,
Line 41, "resistance 95" should be -- resistor 95 --.

Signed and Sealed this

Twenty-ninth Day of October, 2002

Attest:

Attesting Officer

JAMES E. ROGAN
Director of the United States Patent and Trademark Office